United States Patent [19]
Boos et al.

[11] Patent Number: 5,869,543
[45] Date of Patent: Feb. 9, 1999

[54] PROCESS FOR THE SYNTHESIS OF POLYETHYLENE CARBOXYLATE FROM POLYETHYLENE CARBOXYLATE WASTE

[75] Inventors: Frank Boos, Alzenau; Norman Schnittker, Erlensee; Joachim Seelig, Biebergemuend, all of Germany

[73] Assignee: Zimmer Aktiengesellschaft, Germany

[21] Appl. No.: 920,681

[22] Filed: Aug. 29, 1997

[30] Foreign Application Priority Data

Oct. 22, 1996 [DE] Germany .................. 196 43 479.3

[51] Int. Cl.$^6$ ................ C08J 11/04; C08G 63/02
[52] U.S. Cl. ................ 521/48.5; 528/279; 528/280; 528/281; 528/283; 528/285; 528/482; 528/491; 528/495; 528/501; 528/503
[58] Field of Search .............. 521/48.5; 528/279, 528/280, 281, 283, 285, 482, 491, 495, 501, 503; 210/768, 772

[56] References Cited

U.S. PATENT DOCUMENTS

| | | | |
|---|---|---|---|
| 3,070,575 | 12/1962 | Cramer | 528/209 |
| 3,222,299 | 12/1965 | MacDowell | 521/48.5 |
| 4,876,378 | 10/1989 | Van Sickle | 560/78 |
| 5,430,174 | 7/1995 | Shono et al. | 560/78 |

FOREIGN PATENT DOCUMENTS

| | | |
|---|---|---|
| 0 174 062 | 3/1986 | European Pat. Off. . |
| 0 723 951 | 7/1996 | European Pat. Off. . |
| 13537 | 7/1957 | German Dem. Rep. . |
| 1052394 | 3/1959 | Germany . |
| 143323 | 11/1977 | India . |
| 702065 | 3/1966 | Italy . |
| 610136 | 3/1947 | United Kingdom . |
| 775030 | 5/1957 | United Kingdom . |
| WO 93/23465 | 11/1993 | WIPO . |

OTHER PUBLICATIONS

Abstract of Japanese Patent Application No. 41215/70, published Dec. 24, 1970.

*Primary Examiner*—Samuel A. Acquah
*Attorney, Agent, or Firm*—McDonnell Boehnen Hulbert & Berghoff

[57] ABSTRACT

The invention comprises a method for synthesizing polyethylene terephthalate from waste polyethylene terephthalate by cleavage with ethylene glycol and separation of bis(hydroxyethylene) terephthalate from the cleavage mixture with a specific temperature program, recrystallization from water, and esterification and polycondensation with the addition of terephthalic acid.

The invention further comprises a method for synthesis of polyethylene naphthalate from waste polyethylene naphthalate in a similar manner.

11 Claims, No Drawings

PROCESS FOR THE SYNTHESIS OF POLYETHYLENE CARBOXYLATE FROM POLYETHYLENE CARBOXYLATE WASTE

BACKGROUND OF INVENTION

1. Field of the Invention

The invention concerns a process for synthesizing of polyethylene terephthalate (PET) from polyethylene terephthalate waste by cleavage with ethylene glycol, separation of bis(hydroxyethylene) terephthalate (BHET) from the cleavage mixture, and esterification and polycondensation of BHET with terephthalic acid. The invention also concerns a process for producing polyethylene naphthalate (PEN) from polyethylene naphthalate waste by cleavage with ethylene glycol, separation of bis(hydroxyethylene) naphthalate (BHEN) from the cleavage mixture, and esterification and polycondensation of the BHEN with naphthalene dicarboxylic acid.

2. Summary of the Related Art

PET is produced on a large scale in order to manufacture from it products such as textile fibers and packaging materials. After use of these products, considerable quantities of wastes consisting essentially of PET are generated. These wastes often include mixtures with other polymers such as polyvinyl chloride, polyolefins, and other polymers. For ecological as well as economic reasons, it is desirable to recycle the main component of the waste, namely PET, in a production process to permit unlimited use of the newly synthesized PET.

It is known that PET wastes can be cleaved with the help of ethylene glycol, and then the cleavage mixture can be subsequently filtered and subjected to polycondensation while distilling off ethylene glycol and reaction water (British Patent No. 610,136, U.S. Pat. No. 3,222,299, European Patent no. A 174,062). However, these methods are suitable only for pure, unused PET wastes without any additives. Otherwise, contaminated glycolyzation product or PET is obtained that is not suitable for most applications. The delustering agents present in fiber wastes can be removed by treating the cleavage mixture with active carbon, celite, bentonite, etc. and then filtering (Italian Patent No. 702,065). Most contaminants, however, require that the BHET formed by cleavage be subjected to recrystallization from water before renewed polymerization (British Patent No. 610,136, East German Patent No. 13,537, Japanese Patent No. B 70-41,215, Indian Patent No. 143,323, European Patent No. A 723,951) or that the BHET first be hydrolyzed to terephthalic acid and ethylene glycol, which are then purified by crystallization and distillation (European Patent No. A 641,366).

One problem is the separation of BHET from the cleavage mixture prior to the purification step. BHET is obtained as an amorphous to very finely crystalline mass that is difficult to separate. On a very small scale, starting with 1 to 2.5 g PET, BHET yields of 55% to 70% are obtained when using ethylene glycol and approximately 82% when using mother liquor by cooling to 0° C. (German Patent No. B 1,052,394). When cooled rapidly to 90°–100° C. and then cooled slowly to 20° C., yields of approximately 75% are obtained when starting from 20 g PET (Indian Patent No. 143,323). However, these results obtained on a small scale cannot be scaled up to an industrial level—a pasty mixture is obtained, and the liquid containing glycol cannot be separated completely from the paste.

In addition, it is also known that BHET synthesized from the monomer can be reacted with terephthalic acid in the presence of a catalyst to yield PET (British Patent No. 775,030, U.S. Pat. No. 3,070,575). Use of BHET obtained from PET waste is not mentioned.

It is also known that dimethyl naphthalene-2,6-dicarboxylate can be produced by cleavage of PEN with methanol or with ethylene glycol and subsequent ester exchange with methanol (U.S. Pat. Nos. 4,876,378 and 5,430,174). However, production of BHEN is not disclosed.

The object of the present invention is to improve the profitability of the production of high-quality PET from waste PET by cleavage with ethylene glycol and subsequent polycondensation on an industrial scale. In particular, the object of this invention is to provide conditions for the crystallization of BHET in the cleavage mixture so that only large crystals that can be separated almost completely from the liquid phase are formed. The object of this invention is also to produce PEN from waste PEN by cleavage with ethylene glycol and subsequent polycondensation.

SUMMARY OF THE INVENTION

The foregoing objects are achieved by the instant invention, which comprises a method for synthesizing polyethylene terephthalate from waste polyethylene terephthalate by cleavage with ethylene glycol and separation of bis(hydroxyethylene) terephthalate from the cleavage mixture with a specific temperature program, recrystallization from water, and esterification and polycondensation with the addition of terephthalic acid.

The invention further comprises a method for synthesis of polyethylene naphthalate from waste polyethylene naphthalate in a similar manner.

Through the use of a suitable temperature control program during crystallization of BHET or BHEN in the cleavage mixture, the size and thus the separability of the BHET or BHEN crystals can be controlled. The temperature is adjusted in such a way that brief heavy supersaturation of the solution induces nucleation and then at lower supersaturation allows a slow subsequent crystal growth phase. Together with a considerable reduction in concentration in combination with cooling of the solution by adding cold ethylene glycol, a suspension is obtained from which the crystal product can be separated completely, even on an industrial scale. The remaining ethylene glycol content in the crystal phase can be greatly reduced by a suitable choice of separation process. By temperature-guided crystallization, it is also possible to remove impurities such as molecular modifiers of PET or of PEN from the suspension. In combination with filtration of the glycolyzation product, which is not yet crystallized, it is possible to separate most of the PET or PEN impurities like other polymers as well as contaminants of different chemical composition.

The BHET or BHEN crystals thereby obtained can then be subjected to further purification procedures, thereafter reacted with terephthalic acid or naphthalene dicarboxylic acid, respectively, in the presence of conventional catalysts, and then subjected to polycondensation to yield polyethylene carboxylate, as described more fully below.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE PREFERRED EMBODIMENTS

The present invention generally comprises:

a) heating waste polyethylene terephthalate to the boiling point for 3–8 hours with a 9 to 12-fold molar quantity of ethylene glycol (based on one unit of ethylene terephthalate) in the presence of a glycolysis catalyst, and filtering the resulting cleavage mixture at 70°–100° C. and a filter fineness of 1–50 $\mu$m, preferably 10–30 $\mu$m, b) cooling the hot filtrate to a temperature $T_1 = 30°–40°$ C. in less than 10 minutes, preferably less than 3 minutes, by adding a 0.5 to 2-fold quantity by weight, preferably a 1 to 1.5-fold quantity by weight, of ethylene glycol at a temperature of 10°–25° C., and optionally by heat exchange, and then maintaining the filtrate at $T_1$ for 2 to 15 minutes, preferably 2 to 10 minutes, c) heating the filtrate mixture at the temperature $T_1$ at a heating rate of at least 2°–10° C./min to a temperature $T_2 = 35°–45°$ C. that is at least 5° C. higher than $T_1$, and then maintaining the filtrate at $T_2$ for 30 to 120 minutes, preferably 40 to 80 minutes, d) cooling the filtrate mixture at a temperature $T_2$ to a temperature $T_3 = 15°–25°$ C. at a cooling rate of 0.02°–2° C./min, and separating the BHET that crystallizes out from the liquid that contains glycol by centrifugation at a minimum of 1000 g's, preferably 2500 g's to 5000 g's, e) dissolving the BHET thus separated in a 2 to 15-fold, preferably 5 to 10-fold, quantity by weight of water at 50°–100° C., treating the solution at this temperature for 5 to 120 minutes, preferably 20 to 40 minutes, with 0.1 to 10 wt % (based on BHET) of an adsorbent, preferably 1 to 8 wt % active carbon and/or diatomaceous earth, and separating the adsorbent from the BHET solution by filtering or centrifuging at 40°–100° C., f) crystallizing the BHET out of the BHET solution at 0° to 25° C., separating the BHET crystals from the aqueous liquid by filtering or centrifuging, washing with a 0.2 to 15-fold, preferably 1–2-fold, quantity by weight of wash water at 0°–25° C., and optionally drying the BHET to a residual moisture content of 0.001 to 1.0 wt %, preferably 0.1 to 1.0 wt %, and g) mixing the BHET crystals with a 0.2 to 1-fold, preferably 0.5 to 0.9-fold, molar quantity of terephthalic acid and reacting the resultant mixture in the presence of conventional catalysts at 250°–290° C. and 0.5 to 2.0 bar (abs) while separating ethylene glycol and reaction water from the mixture, and then subjecting the mixture to polycondensation at 250° to 300° C. with an incremental reduction in pressure to approximately 1 mbar to yield polyethylene terephthalate.

The process according to this invention is suitable for processing all conventional colorless or colored wastes of PET and modified copolymers thereof (up to approximately 20 wt % comonomer), such as fiber and film wastes and, in particular, shredded PET bottles.

Polyester-soluble zinc, manganese, titanium, cobalt, germanium and/or antimony compounds in the amount of 0.05 to 1.0 wt %, based on waste PET, are suitable glycolysis catalysts. Acetates are preferred, especially zinc acetate in the amount of 0.1 to 0.8 wt %.

The ethylene glycol to be added in steps a) and b) consists of fresh ethylene glycol and/or ethylene glycol recycled internally from step d) and/or step g). Depending on the amount of impurities, e.g., comonomers and oligomers, some or all of the ethylene glycol may be subjected to distillative purification before recycling.

The PET is cleaved at the boiling point of the ethylene glycol mixture, and preferably at atmospheric pressure, i.e., approximately 200° C. It is also possible to use a slightly reduced pressure down to approximately 0.8 bar (abs) or an excess pressure up to approximately 10 bar at the corresponding boiling point.

Through the use of a suitable temperature control program during crystallization of BHET in the cleavage mixture, the size and thus the separability of the BHET crystals can be controlled. Brief heavy supersaturation of the solution should be employed to induce nucleation and low supersaturation employed thereafter to induce slow crystal growth. Together with a considerable reduction in concentration in combination with cooling of the solution by adding cold ethylene glycol, a suspension is obtained from which the crystal product can be separated completely, even on an industrial scale. The remaining ethylene glycol content in the crystal phase can be greatly reduced by a suitable choice of separation process. By temperature-guided crystallization, it is also possible to remove impurities such as molecular modifiers of PET from the suspension. In combination with filtration of the glycolyzation product, which is not yet crystallized, it is possible to separate most of the PET impurities like other polymers as well as contaminants of different chemical composition.

The separated BHET crystals are again dissolved in hot water, and this solution is treated, preferably at atmospheric pressure, with an adsorbent such as active carbon, diatomaceous earth, zeolites or aluminum oxides, which thus removes dyestuffs and colored impurities. The adsorbent is then separated by filtration at a filter fineness of 1 to 50 $\mu$m, especially 10 to 30 $\mu$m, or preferably by centrifuging at a minimum of 100 g's, in particular 1000 g's to 4000 g's. At the same time the short-chain oligomers that are insoluble in hot water and are obtained as a by-product of cleavage are separated.

The separated aqueous solution is then cooled as quickly as possible to 0°–25° C. by external cooling and the BHET is crystallized out. In contrast with crystallization from the cleavage mixture containing ethylene glycol, this method of crystallization from the aqueous phase does not pose any special problems. The BHET crystals can be removed easily from the aqueous phase by filtering at a filter fineness of 1 to 200 $\mu$m, preferably 30 to 100 $\mu$m, or by centrifugation at a minimum of 500 g's, preferably 1000 g's to 3000 g's. If the waste PET contains comonomers with carboxylic groups, then the separated aqueous phase can be subjected to an additional crystallization to recover bis (hydroxyethylene) carboxylates, such as bis (hydroxyethylene) isophthalate, which have a higher solubility than BHET. After the subsequent washing with water or with a solution containing mostly water, the residual moisture content of the BHET crystals is 10 to 30 wt %. The moist BHET crystals can be fed directly into the subsequent esterification step, where the moisture is then expelled together with the reaction vapors. To prevent sticking of the crystals during any intermediate storage that may be necessary, extensive thermal drying under atmospheric pressure or in vacuo is expedient.

The separated aqueous phase is preferably used again for dissolving the BHET crystals in step e). At high concentrations of impurities, a portion of the aqueous phase is preferably removed from the process. The wash water is preferably recycled to the washing process.

The yield of BHET in the batch process is 65 to 95%, generally approximately 80%, based on the BHET theoretically obtainable from waste PET. Any comonomers with hydroxyl groups that may be present in the waste PET will remain largely in the glycol-containing phase of step d) and can optionally be recovered from it.

This BHET has the following properties:

melting point approximately 110° C.

acid value approximately 0.15 meq/kg saponification value: 441–443 mg KOH/g yellowness index: approximately 0.7

This BHET can undergo polycondensation to PET without any further additives. However, this results in large quantities of ethylene glycol that cannot be used further without thermal reprocessing. Polycondensation of BHET with the addition of a corresponding molar amount of terephthalic acid makes it possible to utilize this ethylene glycol to produce PET.

The recovered BHET is reacted first with a stoichiometric quantity or preferably slightly less than a stoichiometric quantity of polyester-grade terephthalic acid in the presence of a conventional catalyst at 250°–290° C. and 0.5 to 2.0 bar (abs), preferably 1.0 bar, while separating the reaction water and excess ethylene glycol, and then polycondensed in a known way at 250°–300° C. with an incremental reduction in pressure until achieving the desired intrinsic viscosity. This may optionally be followed by solid-phase polycondensation. Suitable catalysts include compounds of antimony, titanium, germanium, silicon and/or aluminum, in particular antimony triacetate, in the amount of 50 to 350 ppm antimony. The separated ethylene glycol can be recycled back to step a) and/or step b) after distillative separation of the reaction water.

If copolyesters are desired, the terephthalic acid may be partially replaced by other dicarboxylic acids, preferably isophthalic acid or 2,6-naphthalene dicarboxylic acid. It is also possible to add other diols such as diethylene glycol or 1,4-cyclohexanedimethanol. The sum of co-monomers should not exceed approximately 20 wt %, based on BHET. In addition, conventional polyester additives such as stabilizers, antioxidants, chain branching agents, delustering agents and/or coloring agents may also be added.

The process according to this invention may be carried out as a continuous or discontinuous process. It is also possible to carry out steps a) to f) discontinuously and step g) continuously. In this case the BHET obtained in step f) is dried to a maximum residual moisture content of 1.0 wt % and stored temporarily until the amount available is sufficient for continuous further processing.

Furthermore, the present invention also comprises producing PEN from waste PEN by cleavage with ethylene glycol, separation of BHEN from the cleavage mixture, and subsequent polycondensation.

It is surprisingly possible to cleave PEN with ethylene glycol and isolate BHEN from the cleavage mixture under exactly the same conditions as described above for PET. Polycondensation of BHEN with 2,6-naphthalene dicarboxylic acid to PEN does not require any fundamentally different conditions. However, PEN of a satisfactory color is obtained only by using sufficiently pure naphthalene dicarboxylic acid. The 2,6-naphthalene dicarboxylic acid available on an industrial scale with a purity of only about 85% leads to PEN with a brownish discoloration. Laboratory experiments indicate that a purity of more than 95% is necessary.

EXAMPLES

The physical properties of the products reported here were determined as follows:

1. BHET or BHEN

The melting point was determined by DSC (differential scanning calorimetry) using a device from Mettler at a heating rate of 10° C./min.

The acid value was determined by potentiometric titration of a solution of BHET or BHEN in N,N-dimethyl formamide with 0.1N ethanolic potassium hydroxide solution.

The saponification value was determined by saponification with 0.5N potassium hydroxide solution in 1-propanol/ethylene glycol (4:1 parts by volume) and back titration.

The yellowness index was determined by measuring the color of the BHET specimen with three photocells preceded by an upstream red, green or blue filter in a three-color or tristimulus colorimeter (X, Y and Z values), where $$\text{yellowness index} = 100 \cdot \left[ \frac{(1.277 \cdot X - 1.06 \cdot Z)}{Y} \right]$$

2. PET

The intrinsic viscosity (I.V.) was measured at 25° C. on a solution of 500 mg polyester in 100 mL of a mixture of phenol and 1,2-dichlorobenzene (3:2 parts by weight).

Diethylene glycol (DEG) was determined by gas chromatography in an ester exchange mixture of 1 g polyester with 30 mL methanol and 50 mg/L zinc acetate obtained in a Carius tube at 200° C.

The COOH end group concentration was determined by photometric titration of a solution of the polyester in a mixture of o-cresol and chloroform (70:30 parts by weight) against bromothymol blue with 0.05N ethanolic potassium hydroxide solution.

The turbidity was measured in "nephelometric turbidity units" (NTU) on a 10 wt % solution of polyester in phenol/1,2-dichlorobenzene (3:2 parts by weight) with a nephelometer from Hach (model XR according to U.S. Pat. No. 4,198,161) in a cell with a diameter of 22.2 mm. The intensity of the scattered light was measured in comparison with a standard formazine solution and subtracting the value of the pure solvent (approximately 0.3 NTU).

The Hunter color value b was measured on polyester granules that were crystallized at 135°±5° C. for one hour in a drying cabinet and then ground (<400 μm). The color value was determined by measuring the color of the polyester sample in a three-color calorimeter with three photocells with upstream red, green and blue filters (X, Y and Z values), where $$b = \frac{7.0 \cdot (Y - 0.8467 \cdot Z)}{\sqrt{Y}}$$

EXAMPLE 1

100 kg shredded PET bottles, 323 kg ethylene glycol, and 0.5 kg zinc acetate dihydrate were placed in a stirred vessel equipped with a reflux condenser and maintained at boiling for six hours. After cooling to approximately 80° C., the cleavage mixture was filtered through a 20 μm filter into a jacketed vessel with 423 kg ethylene glycol at approximately 20° C. At the same time, cooling water at a temperature of approximately 12° C. was circulated through the jacket of the vessel. After approximately three minutes, the temperature of the filtrate-ethylene glycol mixture had dropped to 35° C. The cooling water was turned off, and after five minutes it was replaced by a circulating heating medium at a temperature of approximately 60° C. After approximately one minute, the temperature of the filtrate mixture had increased to 40° C. The circulation of the heating medium was adjusted to maintain a temperature of 40° C. for 60 minutes. Then the system was again switched to cooling water at approximately 12° C. After reaching a temperature of approximately 20° C., the filtrate mixture was transferred to a centrifuge and the crystal product was centrifuged out of the liquid containing glycol at 3500 g's.

This yielded 235 kg crystal product with a residual ethylene glycol content of 30 wt %, which was dissolved in 2350 kg (1:10) hot water at approximately 98° C. while stirring. The solution was mixed with 9.4 kg (4 wt %) diatomaceous earth, type FW-14 from United Minerals, and 4.7 kg active carbon, type SA-X 300 from Norit, and stirring was continued for 30 minutes at approximately 98° C. After cooling the solution to approximately 80° C., diatomaceous earth and active carbon were filtered out through a 20 μm filter and the filtrate was allowed to cool to room temperature (approximately 20° C.). After a dwell time of approximately 10 minutes (after filtration), the crystallized BHET was separated by centrifugation at 2000 g's and the crystal mass was washed with an equal amount of water at room temperature and then dried to a residual moisture content of 0.5 wt % at 80° C. in a vacuum drying cabinet.

This yielded 103.2 kg (based on dry weight) BHET crystals with the following properties:
   melting point: 110.6° C.
   acid value: 0.16 meq/kg
   saponification value: 442.0 mg KOH/g
   yellowness index: 0.7

The 103.2 kg BHET were esterified for 60 minutes together with 45 kg terephthalic acid and 55 g antimony triacetate at atmospheric pressure and a temperature rising to 270° C. in a stirred reactor equipped with a distillation column and then precondensed for 30 minutes while the pressure was gradually reduced to 50 mbar and the temperature increased to 275° C. The precondensate was transferred to a polycondensation reactor, the pressure was lowered within 45 minutes to less than 2 mbar (abs), and then the precondensate was subjected to polycondensation for 130 minutes at temperatures rising to approximately 280° C. Next the polyester was removed from the reactor and granulated. The PET granules had the following properties:
   intrinsic viscosity: 0.686 dL/g
   DEG content: 0.76 wt %
   COOH end groups: 19 meq/kg
   b color value: +2.1
   turbidity: 3 NTU

EXAMPLE 2

In an autoclave, 100 kg chopped PEN wastes, 255 kg ethylene glycol and 0.5 kg zinc acetate dihydrate were placed as the starting material and kept at the boil for six hours at a pressure of 4.5 bar. After cooling to approximately 100° C., the cleavage mixture was filtered through a 20 μm filter into a jacketed vessel containing 355 kg ethylene glycol at approximately 20° C. At the same time, cooling water at approximately 12° C. was circulated through the jacket of the vessel. After approximately 4 minutes, the temperature of the filtrate-ethylene glycol mixture had dropped to 35° C. Further work-up was performed under the same conditions as in Example 1.

This yielded 140 kg crystal product with a residual ethylene glycol content of 30 wt %, which was dissolved in 1400 kg hot water (at approximately 98° C.) and then treated by the same procedure as described in Example 1.

This yielded 94.2 kg BHEN crystals (based on dry weight) with the following properties:
   melting point: 139° C.
   saponification value: 365.3 mg KOH/g
   ash content: <0.05 wt %

The foregoing examples are provided for illustrative purposes only and are not intended, nor should they be construed, as limiting the invention in any manner. Those skilled in the art will appreciate that variations and modifications of the foregoing examples can be made without exceeding the spirit or scope of the present invention.

We claim:

1. A method for synthesis of polyethylene carboxylate from waste polyethylene carboxylate, comprising
   a) heating waste polyethylene carboxylate with excess ethylene glycol in the presence of a glycolysis catalyst until cleavage of the polyethylene carboxylate, and filtering the hot cleavage mixture,
   b) cooling the hot filtrate as quickly as possible to a temperature $T_1$ of 30°–40° C. by adding cold ethylene glycol and optionally by heat exchange, and maintaining the temperature $T_1$ for 2 to 15 minutes,
   c) heating the filtrate mixture as quickly as possible to a higher temperature $T_2$ of 35°–45° C., and maintaining the temperature $T_2$ for at least 30 minutes,
   d) cooling the filtrate mixture slowly at a cooling rate of not more than 2° C./min to a temperature $T_3$ of 15°–25° C., and separating the crystallized bis (hydroxyethylene) carboxylate (BHEC) from the liquid containing glycol,
   e) dissolving the BHEC thus separated in hot water, treating the hot solution with an absorbent and separating the adsorbent from the hot aqueous solution,
   f) crystallizing the BHEC out of the aqueous solution at a temperature of 0°–25° C., separating the BHEC crystals from the aqueous liquid, washing the BHEC crystals with cold wash water and optionally drying the BHEC crystals,
   g) reacting the BHEC crystals in the presence of conventional catalysts with the 0.2 to 1-fold molar quantity of the same dicarboxylic acid as those forming the BHEC, while separating ethylene glycol and reaction water, and polycondensing the reaction mixture under reduced pressure to polyethylene carboxylate.

2. The method according to claim 1, wherein the waste polyethylene carboxylate is polyethylene terephthalate or polyethylene naphthalate.

3. The method according to claim 1, comprising
   a) heating waste polyethylene terephthalate with a 7 to 15-fold molar quantity of ethylene glycol at the boiling point for 3 to 8 hours in the presence of a glycolysis catalyst, and filtering the resulting cleavage mixture at 70°–100° C. and a filter fineness of 1 to 50 μm,
   b) cooling the hot filtrate to a temperature $T_1$ of 30°–40° C. in less than 10 minutes by adding a 0.5 to 2-fold quantity by weight of ethylene glycol at a temperature of 10°–25° C., and optionally by heat exchange, and maintaining the temperature at $T_1$ for 2 to 15 minutes,
   c) heating the filtrate mixture at a heating rate of at least 2°–10° C./min to a temperature $T_2$ of 35°–45° C. that is at least 5° C. higher then $T_1$, and maintaining the temperature at $T_2$ for 30 to 120 minutes, d) cooling the filtrate mixture to a temperature $T_3$ of 15°–25° C. at a cooling rate of 0.02°–2° C./min, and separating the crystallized BHET from the liquid that contains glycol by centrifugation at a minimum of 1000 g's, e) dissolving the BHET thus separated in a 2 to 15-fold quantity by weight of water at 50°–100° C., treating the solution at this temperature for 5 to 120 minutes with 0.1 to 10 wt % (based on BHET) of an adsorbent, and separating the adsorbent from the BHET solution at 40°–100° C. by filtering or centrifuging, f) crystallizing the BHET out of the BHET solution at 0 to 25° C., separating the BHET crystals from the aqueous liquid by filtering or centrifuging, washing the BHET crystals with a 0.2 to 15-fold quantity by weight of wash water at 0°–25° C., and optionally drying to a residual moisture content of 0.001 to 1.0 wt %, g) mixing the BHET crystals with a 0.2 to 1-fold molar quantity of terephthalic acid, reacting the BHET and terephthalic acid mixture in the presence of conventional catalysts, at 250°–290° C. and 0.5 to 2.0 bar (abs), separating ethylene glycol and reaction water, and then subjecting to polycondensation at 250° to 300° C. with an incremental reduction in pressure to approximately 1 mbar to yield polyethylene terephthalate.

4. The method according to claim 1, comprising a) heating waste polyethylene naphthalate with a 7 to 15-fold molar quantity of ethylene glycol at the boiling point for 3–8 hours in the presence of a glycolysis catalyst, and filtering the resulting cleavage mixture at 70°–100° C. and a filter fineness of 1–50 μm, b) cooling the hot filtrate to a temperature $T_1$ of 30°–40° C. in less than 10 minutes by adding a 0.5 to 2-fold quantity by weight of ethylene glycol at a temperature of 10°–25° C. and optionally by heat exchange, and maintaining the Temperature $T_1$ for 2 to 15 minutes, c) heating the filtrate mixture at a heating rate of at least 2°–10° C./min to a temperature $T_2$ of 35°–45° C. which is at least 5° C. higher than $T_1$ and maintaining the temperature at $T_2$ for 30 to 120 minutes, d) cooling the filtrate mixture to a temperature $T_3$ of 15°–25° C. at a cooling rate of 0.02°–2° C./min, and separating the crystallized BHEN from the liquid that contains glycol by centrifugation at a minimum of 1000 g's, e) dissolving the BHEN thus separated in a 2-fold to 15-fold quantity by weight of water at 50° C. to 100° C., treating the solution with 0.1 to 10 wt % (based on BHEN) of an adsorbent for 5 to 120 minutes at this temperature, and separating the adsorbent from the BHEN solution at 40°–100° C. by filtering or centrifuging, f) crystallizing the BHEN out of the BHEN solution at 0° to 25° C., separating the BHEN crystals from the aqueous liquid by filtering or centrifuging, washing the BHEN crystals with a 0.2-fold to 15-fold quantity by weight of wash water at 0° C. to 25° C. and optionally drying to a residual moisture content of 0.001 wt % to 1.0 wt %, g) mixing the BHEN crystals with a 0.2-fold to 1-fold molar quantity of naphthalene dicarboxylic acid, reacting the mixture at 250° C. to 290° C. and 0.5 to 2.0 bar (abs) in the presence of conventional catalysts, while ethylene glycol and the reaction water are separated and then subjecting to polycondensation at 250° C. to 300° C. with an incremental reduction in pressure to approximately 1 mbar to yield polyethylene naphthalate.

5. The method according to claim 1, wherein the ethylene glycol in step a), step b), or both consists at least partially of the liquid containing glycol separated in step d).

6. The method according to claim 5, wherein the liquid containing glycol is purified by distillation before being reused.

7. The method according to claim 1, wherein the water in step e) consists at least partially of the aqueous liquid separated in step f).

8. The method according to claim 1, wherein the wash water is recycled within step f).

9. The method according to claim 1, wherein the ethylene glycol separated in step g) is recycled to step a), step b), or both after distillative separation of the reaction water.

10. The method according to claim 1, wherein the dicarboxylic acid added in step g) is partially replaced by another dicarboxylic acid in the amount of 0 to 20 wt % based on BHEC.

11. The method according to claim 1, wherein the glycolysis catalyst in step a) is a polyester-soluble zinc, manganese, titanium, cobalt, germanium or antimony compound, or combinations thereof, in the amount of 0.05 to 1.0 wt % based on waste polyethylene carboxylate.

* * * * *